US005836899A

United States Patent [19]
Reilly

[11] Patent Number: 5,836,899
[45] Date of Patent: Nov. 17, 1998

[54] VIBRATING MASSAGE SYSTEM FOR FOOTWEAR

[76] Inventor: Peter C. Reilly, Three Hanover Sq., New York, N.Y. 10004

[21] Appl. No.: 769,838

[22] Filed: Dec. 20, 1996

[51] Int. Cl.[6] ................................ A61H 1/00; A61F 5/14
[52] U.S. Cl. ................................ 601/46; 601/70; 36/141
[58] Field of Search ................................ 601/46, 49–51, 601/53, 57–60, 66, 67, 70, 78, 79; 36/141, 71, 43, 44

[56] References Cited

U.S. PATENT DOCUMENTS

| | | | |
|---|---|---|---|
| 3,731,674 | 5/1973 | Parvin | 601/70 X |
| 4,232,459 | 11/1980 | Vaccari | 36/71 |
| 4,802,463 | 2/1989 | Rojas | 601/70 |
| 5,113,850 | 5/1992 | Larremore et al. | 601/46 |
| 5,592,759 | 1/1997 | Cox | 36/141 |

FOREIGN PATENT DOCUMENTS

| | | | |
|---|---|---|---|
| 3842913 | 6/1990 | Germany | 36/141 |

*Primary Examiner*—Danton D. DeMille
*Attorney, Agent, or Firm*—Charles E. Baxley, Esq.

[57] ABSTRACT

A massage system incorporates a battery operated power supply which is mounted in a compartment formed in the tongue of a shoe. The power supply is connected to vibrators which are mounted in circular beds formed in the sole of the shoe. The power supply and the vibrators are connected by wires which are concealed in a flap formed in the upper portion of the shoe. The wires are also disposed in air canals which are formed in the sole of the shoe. The location of the power supply in the tongue of the shoe maintains the normal balance of the shoe and enables a user to benefit from vibrating massage while standing, sitting, walking or running.

17 Claims, 7 Drawing Sheets

VIBRATING MASSAGE SYSTEM FOR FOOTWEAR

BACKGROUND OF THE INVENTION

The present invention relates generally to footwear and, more particularly, to a vibrating massage system for footwear.

THE PRIOR ART

The prior art related to footwear includes various configurations of inner soles which are intended to aid the user by applying pressure to specific portions of the sole of the foot. These inner soles rely on a combination of pads, protrusions or curved portions to apply various types of pressure. All of these devices are static in nature and rely on the application of pressure by the user's foot.

Despite the various developments of the prior art, there remains a need for an apparatus which can apply a vibrating massage to the soles of a user's feet.

OBJECTS AND SUMMARY OF THE INVENTION

It is an object of the present invention to provide a vibrating massage system for footwear which is capable of delivering a dynamic, vibrating massage to the soles of a user's feet.

Another object of the present invention is to provide a vibrating massage system for footwear which can be easily installed or replaced by a user.

Another object of the present invention is to provide a vibrating massage system for footwear which can withstand the forces applied during running.

Another object of the present invention is to provide a vibrating massage system for footwear which incorporates cooling air channels.

Another object of the present invention is to provide a vibrating massage system for footwear which provides convenient access to a control button for ease of operation.

Another object of the present invention is to provide a vibrating massage system for footwear which maintains the normal balance of the footwear.

Another object of the present invention is to provide a vibrating massage system for footwear which incorporates multi-speed vibrating action.

Another object of the present invention is to provide a vibrating massage system for footwear which incorporates an automatic shut-off.

Yet another object of the present invention is to provide a vibrating massage system for footwear which incorporates a relatively small number of component parts which can be manufactured economically resulting in relatively low overall cost and reliable long term operation.

The foregoing and other objects and advantages of the present invention will appear more clearly hereinafter.

In accordance with the present invention there is provided a guard for a vibrating massage system for footwear which includes a power supply which is mounted in a compartment formed in the tongue of a shoe and vibrators which are disposed in circular beds-which are formed in the sole of the shoe. The power supply includes a battery compartment and is operated by pushing on a control button cover which is mounted on the upper surface of the tongue. The power supply and the vibrators are connected by wires which pass under a concealment flap which is formed on the upper portion of the shoe. The wires pass through a series of air canals which are formed in the sole of the shoe. The location of the power supply within the tongue of the shoe maintains the normal balance of the shoe and enables the user to benefit from a relaxing massage while standing, sitting, walking or even running.

DESCRIPTION OF THE DRAWINGS

Other important objects and advantages of the invention will be apparent from the following detailed description, taken in connection with the accompanying drawings, in which.

DETAILED DESCRIPTION OF THE INVENTION

Figure 1:
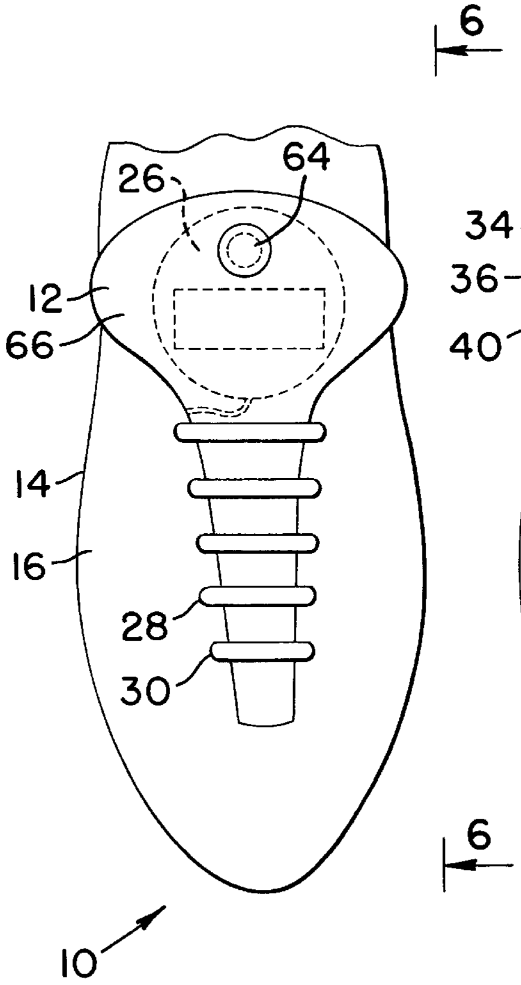
FIG. 1 is a fragmentary top view of a shoe which incorporates a vibrating massage system for footwear, made in accordance with the present invention, with internal components of the system shown in broken lines.

With reference to the drawings, wherein like reference numbers designate like or corresponding parts throughout, there is shown in FIGS. 1–15 a vibrating massage system for footwear 10 made in accordance with the present invention.

The vibrating massage system 10 includes a tongue 12, an upper member 14 of a shoe 16, a sole 18, a plurality of vibrators 20, 22, 24 and a power supply 26. The system 10 is shown incorporated in the shoe 16 which may be a conventionally constructed sneaker, running shoe or walking shoe in which the upper member 14 is attached to the sole 18 using conventional attachment techniques such as adhesive bonding or stitching. The upper member 14 incorporates a conventional closure 28 in the form of laces 30 as is shown in FIGS. 1 and 2.

Figure 2:
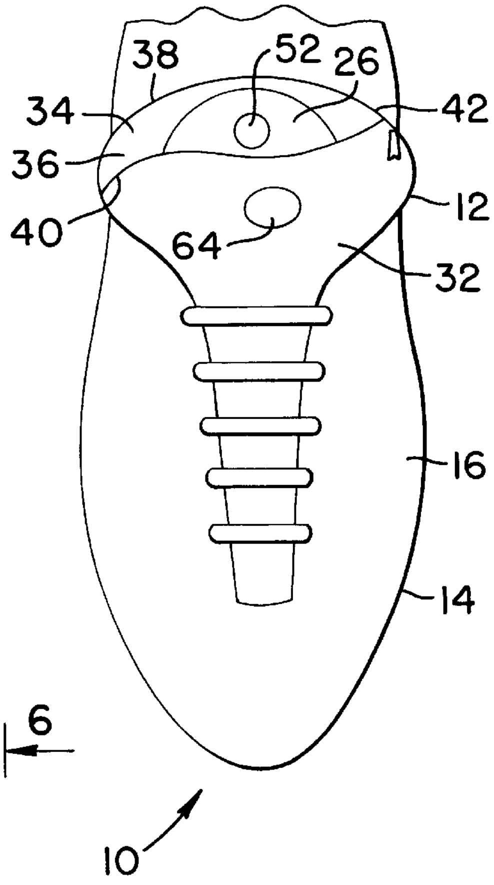
FIG. 2 is a fragmentary top view of a shoe, similar to FIG. 1, with the tongue compartment shown partially opened to reveal internal components.

As is shown in FIGS. 1 and 2, the tongue 12 has an upper layer 32 and a lower layer 34 and the upper 32 and lower layers 34 form a pocket 36 or compartment. Marginal edges 38, 40 of the upper and lower layers 32, 34 are sealed using a hook and loop fastener, such as is sold under the trademark VELCRO or using a conventional zipper closure 42 as is best shown in FIG. 2.

The power supply 26 is mounted in the compartment 36 formed in the tongue 12, as is best shown in FIG. 2. The power supply 26 is shown removed from the system 10 in FIGS. 3–5 for purposes of clarity of illustration. The power supply 26 is generally cylindrical in configuration and includes a generally flat and circular upper surface 44, a generally flat and circular lower surface 46 and a side wall 48. A hook and loop fastener 50 is disposed on the lower surface 46 for the purpose of mounting the power supply 26 on the lower layer 34 of the tongue 12. The upper surface 44 of the power supply 26 includes a control button 52 and a battery compartment 54.. The side wall 48 includes an exit port 56 which allows exit of wires 58, 60, 62 to the vibrators 20, 22, 24 in a manner which will be presently described in detail.

The control button 52 is mounted in a facing relationship with a control button cover 64 which is disposed on the top surface 66 of the upper layer 32 of the tongue 12. Manual pressure by a user on the control button cover 64 is transmitted to the control button 52 on the power supply 26 for the purpose of turning the power supply 26 on and off and also for the purpose of selecting the electrical output of the power supply 26.

Figure 3:
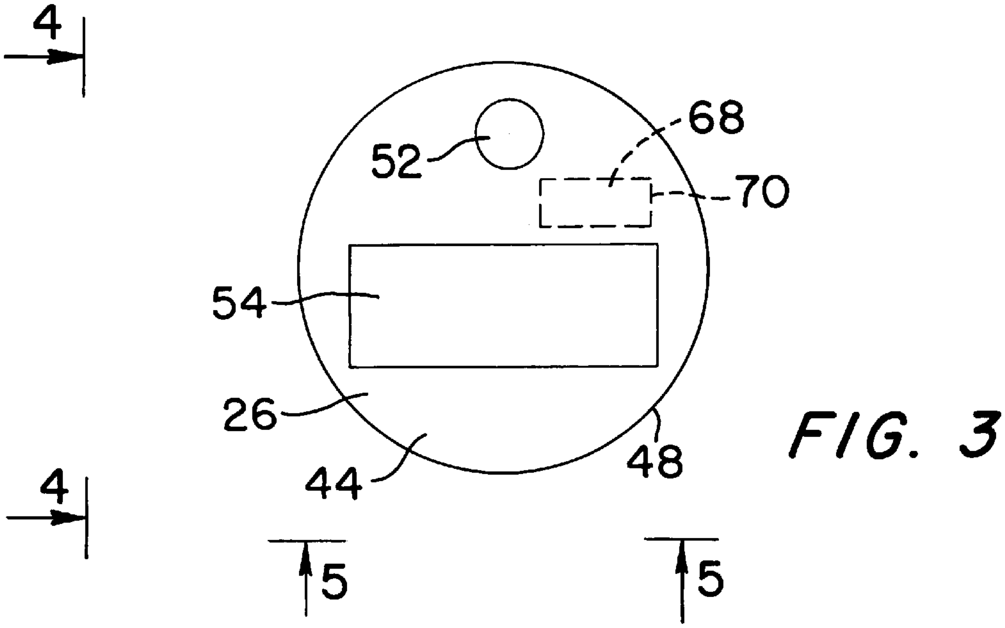
FIG. 3 is a top view of the power supply of the system of FIG. 1 with the power supply shown removed from the system.
Figure 4:
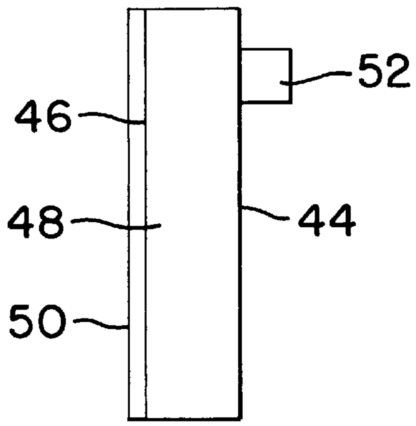
FIG. 4 is a side elevational view of the power supply of FIG. 3 taken along line 4—4 of FIG. 3.
Figure 5:
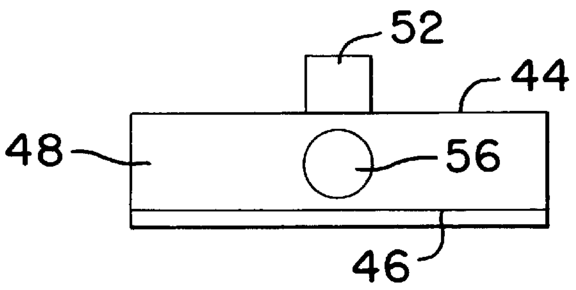
FIG. 5 is another side elevational view of the power supply of FIG. 3, taken along line 5—5 of FIG. 3.

The power supply 26 includes an electronic control unit 63 which is conventional in construction and which is shown schematically in broken lines 20 in FIG. 3. The control unit 68 selectively provides three speeds of vibrator 20, 22, 24 operation (low, medium and high) which can be selected by selectively pressing the control button cover 64 a pre-selected number of times. The electric control unit 68 also incorporates a timer which automatically shuts off power to the vibrators 20, 22, 24 for a pre-selected period of time after a pre-selected period of operation. An appropriate duty cycle for the system 10 has been developed in which power to the vibrators 20, 22, 24 is shut off for a period in the order of five minutes after every ten minutes of operation.

Figure 6:
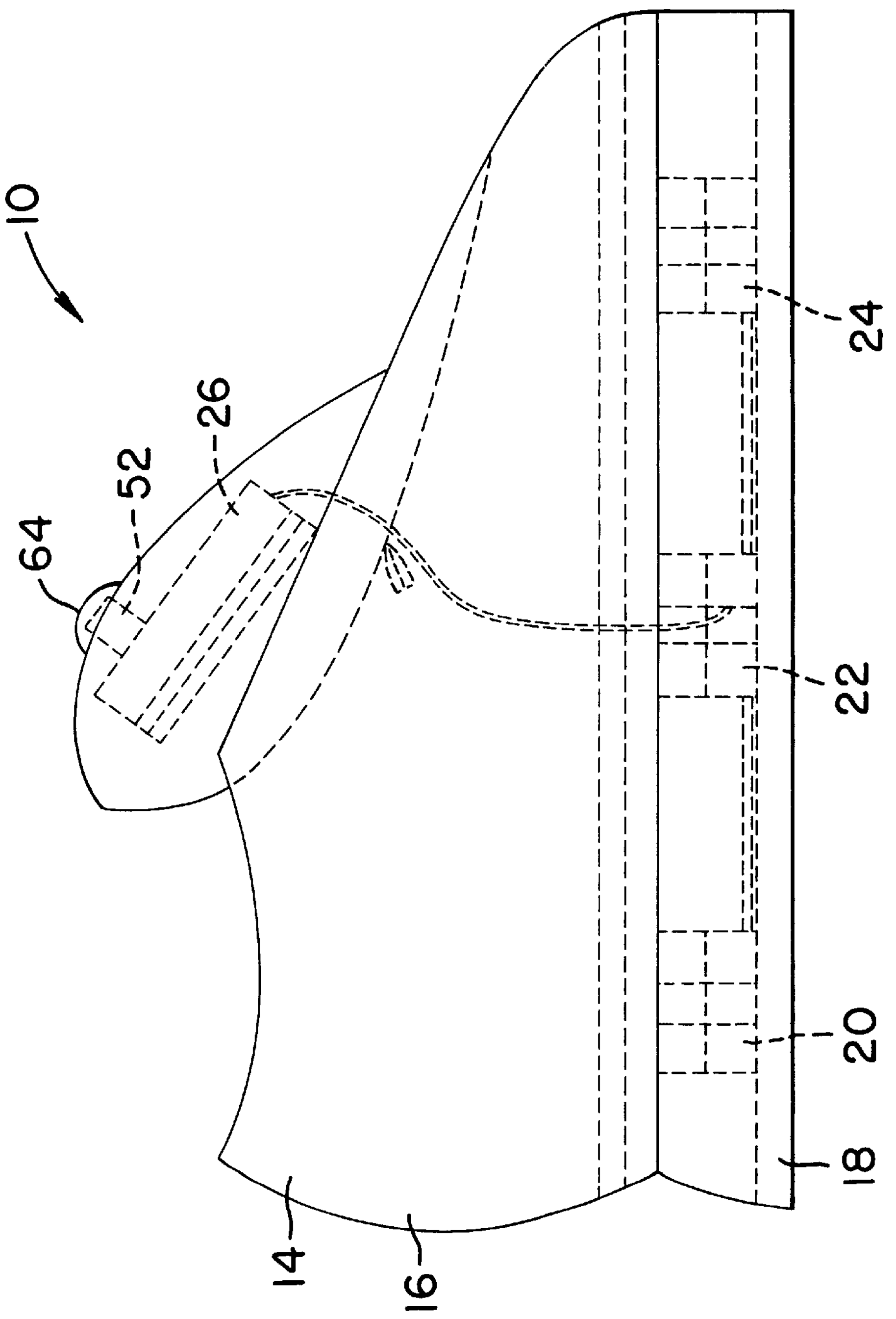
FIG. 6 is a side elevational view of the shoe of FIG. 1, taken along line 6—6 of FIG. 1.
Figure 7:
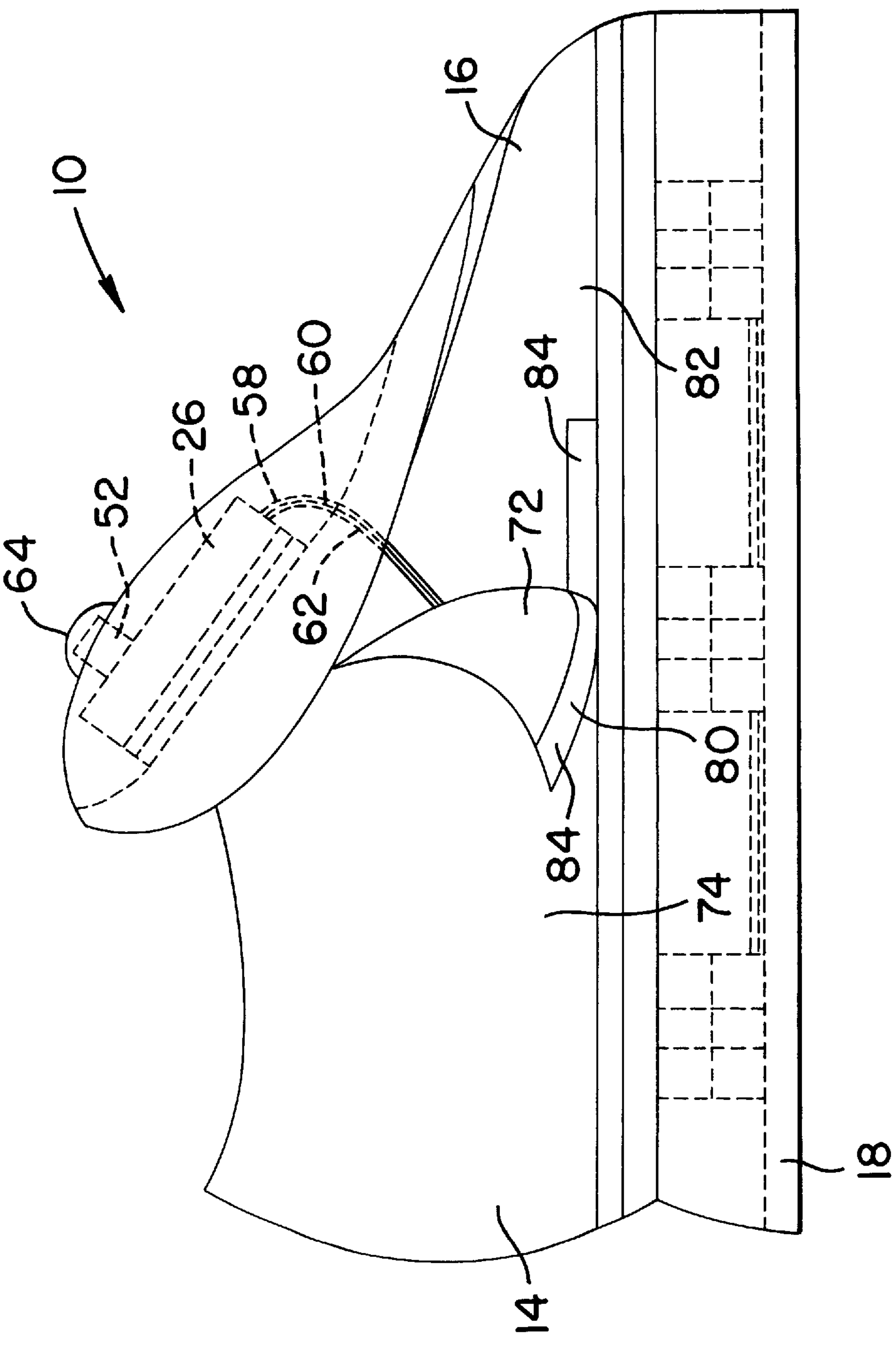
FIG. 7 is a side elevational view similar to FIG. 6 showing the flap on the inner arch wall of the shoe partially open.

As is shown in FIGS. 6 and 7, the wires 58, 60, 62 which connect the power supply 26 to the vibrators 20, 22, 24 are concealed in a flap 72 which is formed on the inner wall 74, or arch wall, of the upper member 14. The lower edge 80 of the flap 72 is connected to the lower edge 82 of the upper member 14 by a hook and loop fastener 84.

Figure 8:
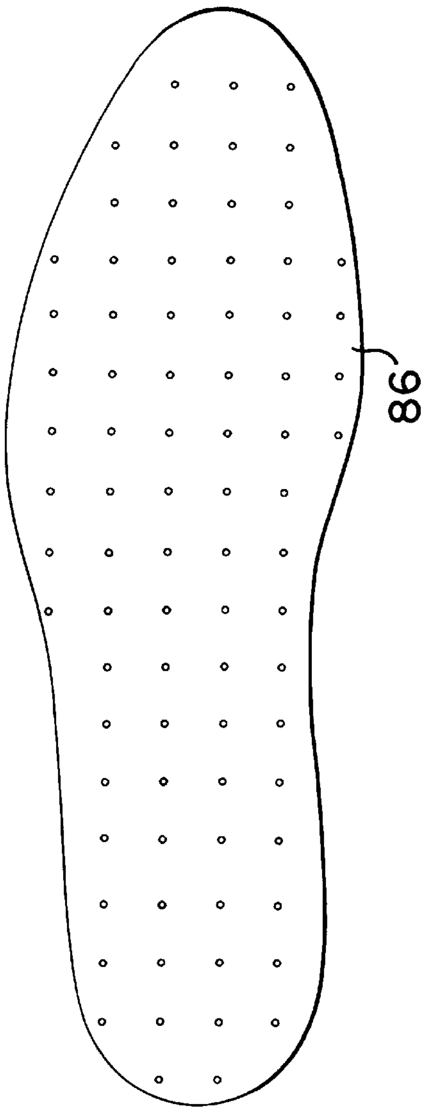
FIG. 8 is a plan view of a perforated inner sole with the inner sole shown removed from the shoe of FIG. 1.
Figure 9:
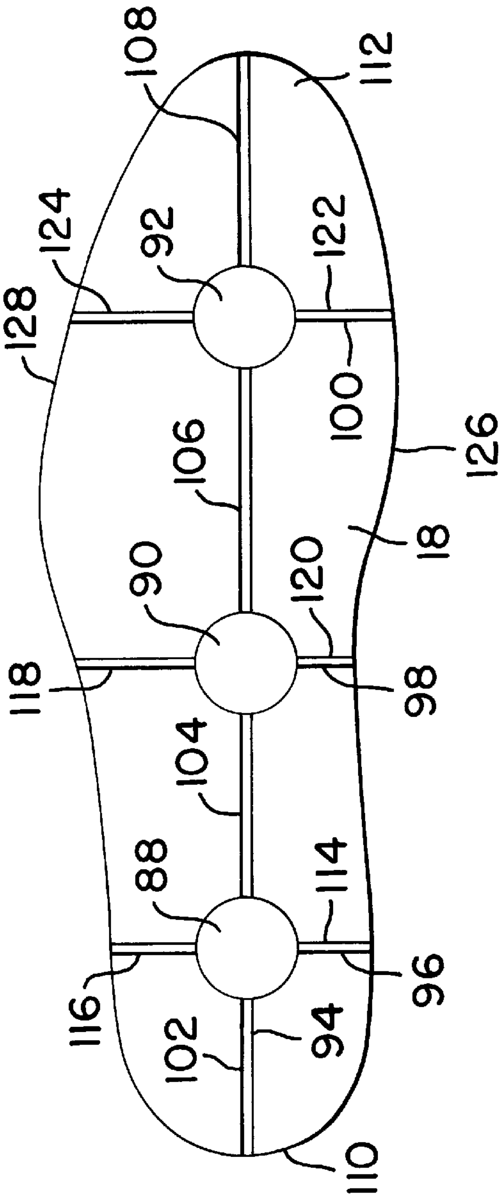
FIG. 9 is a top plan view of the base sole of the shoe of FIG. 1.
Figure 10:
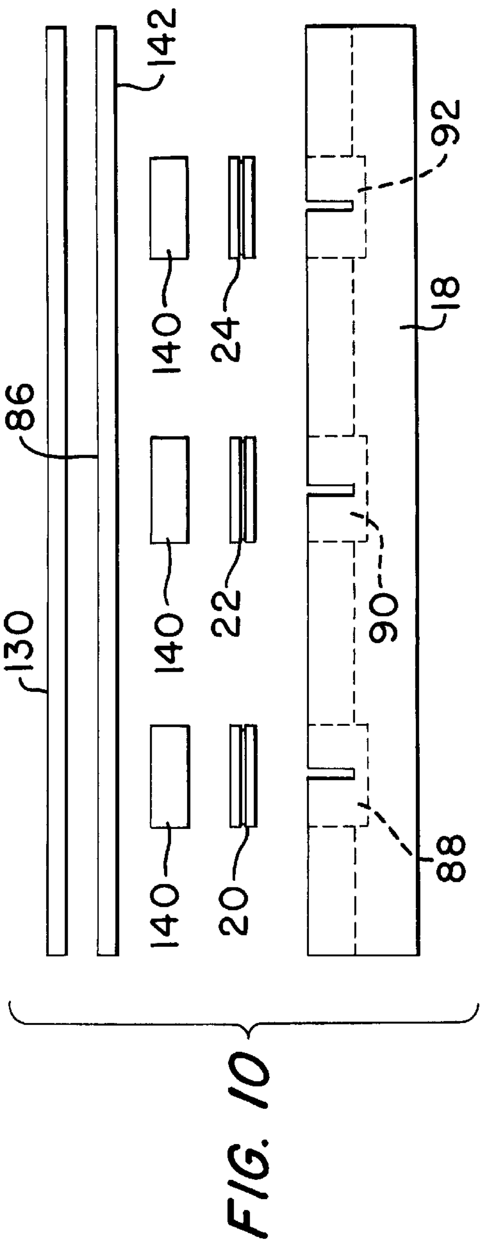
FIG. 10 is an exploded elevational view of the components of the system of FIG. 1.
Figure 11:
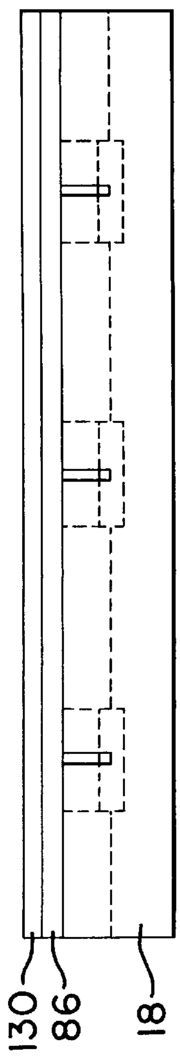
FIG. 11 is an elevational view of the components of the system of FIG. 1.
Figure 12:
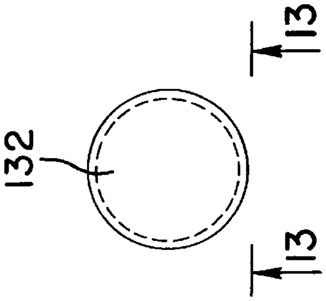
FIG. 12 is a top plan view of a vibrator component of the system of FIG. 1.
Figure 13:
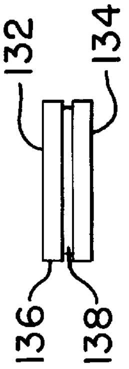
FIG. 13 is a side elevational view of the vibrator of FIG. 12, taken along line 13—13 of FIG. 12.

The system 10 includes a perforated insole 86 which is shown removed from the system 10 in FIG. 8. The perforated insole 86 covers the sole 18 which is best shown in FIGS. 9–11. The sole 18 includes three circular beds 88, 90, 92 for the vibrators 20, 22, 24 and a plurality of air canals 94, 96, 98, 100. The air canal 94 is disposed longitudinally and segments 102, 104, 106, 108 of this air canal 94 connect the heel 110 and toe portions 112 of the sole 18 and the three circular beds 88, 90, 92.

Air canals 96, 98, 100 are disposed laterally and segments 114, 116, 118, 120, 122, 124 connect the circular beds 88, 90, 92 with lateral edges 126, 128 of the sole 18.

Figure 14:
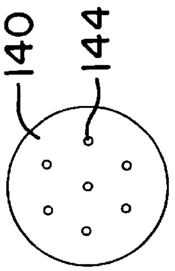
FIG. 14 is a top plan view of the perforated filler component of the system of FIG. 1.

As is best shown in FIG. 10, the system 10 includes a standard conventional insole 130 which covers the perforated insole 86 which was shown in FIG. 8. The perforated insole 86 covers the sole 18 and covers the vibrators 20, 22, 24 which are located in the circular beds 88, 90, 92. The vibrators 20, 22, 24 are each generally cylindrical in configuration and include a top wall 132, a bottom wall 134 and a side wall 136. The side wall 136 includes a groove 138. A generally cylindrical filler member 140 is disposed between the top wall 132 of the vibrators 20, 22, 24 and the lower surface 142 of the perforated insole 86. The filler member 140 has perforations 144 as is shown in FIG. 14. The filler member 140 transmits the vibrating motion of the vibrators 20, 22, 24 to the sole 86.

Figure 15:
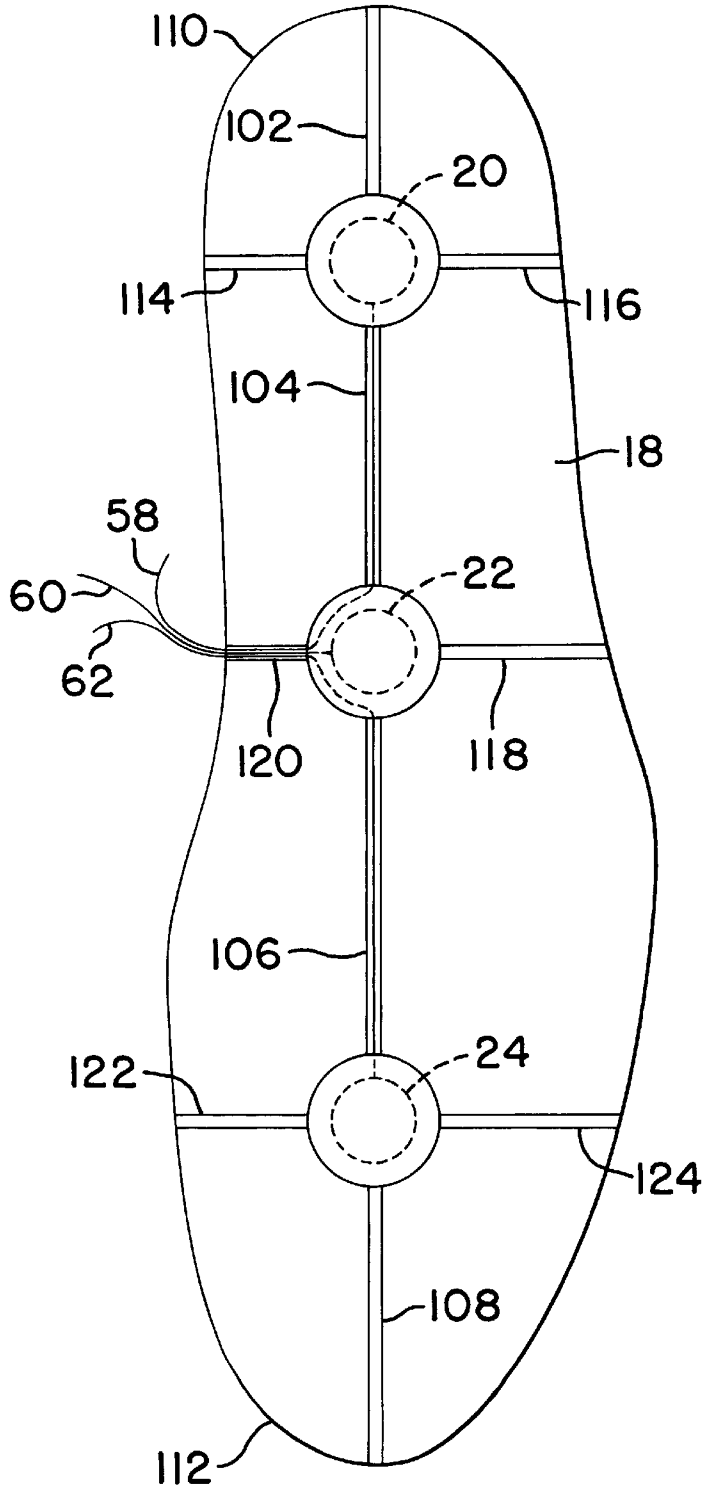
FIG. 15 is a top plan view of the sole base of the system of FIG. 1 with the vibrators shown in broken lines.

As is shown in FIG. 15, the wires 58, 60, 62 which connect the vibrators 20, 22, 24 and the power supply 26 are disposed in the air canal segments 104, 106, 120. The location of the wires 58, 60, 62 in the air canals 104, 106, 120 prevents chafing or damage to the wires 58, 60, 62 during use of the system 10.

During operation, a user need only reach down and push on the control button cover 64 to operate the power supply 26 and thereby provide a relaxing and convenient massage to the soles of the feet. The system 10 can be used while the user is walking, running or standing still. The location of the power supply 20 within the tongue 12 allows the weight of the power supply 26 to be borne directly by the upper part of the foot. This arrangement maintains the balance of the shoe 16 and does not interfere with the user's normal walking or running gait. The entire system 10 is easily removable from the shoe 16 for repair or replacement of individual components and the air canals 94, 96, 98, 100 provide ventilation to prevent overheating and increase the longevity of the vibrators 20, 22, 24 while also providing cooling air to the user's feet.

The foregoing specific embodiment of the present invention as set forth in the specification herein is for illustrative purposes only. Various deviations and modifications can be made within the spirit and scope of this invention, without departing from the main theme thereof.

I claim:

1. A vibrating massage system for footwear comprising:

a tongue;

an upper member with said upper member having an arch wall;

a sole with said sole having an inner surface, an outer surface, a heel portion and a toe portion;

vibrator means mounted on said inner surface of said sole;

power supply means mounted on said tongue;

battery means mounted on said tongue;

control means mounted on said tongue;

electrical connection means with said electrical connection means connecting said vibrator means, said power supply means, said battery means and said control means.

2. A vibrating massage system according to claim 1, in which said inner surface of said sole further comprises a cavity portion and with said vibrator means mounted in said cavity portion.

3. A vibrating massage system according to claim 1, in which said battery means are mounted in said power supply means.

4. A vibrating massage system according to claim 1, in which said tongue comprises:

an upper layer;

a lower layer; and zipper means attaching selected marginal edges of said upper and lower layers thereby forming a compartment therebetween, with said power supply means disposed in said compartment.

5. A vibrating massage system according to claim 4, further comprising:

fastener means with said fastener means disposed removably attaching said power supply means to said lower layer of said tongue.

6. A vibrating massage system according to claim 5, in which said fastener means comprises hook and loop fastener means.

7. A vibrating massage system according to claim 1, in which said control means are mounted on said power supply means.

8. A vibrating massage system according to claim 4, in which said control means comprises:

a control button mounted on said power supply means; and a control button cover mounted on said upper layer of said tongue.

9. A vibrating massage system according to claim 1, in which said vibrator means comprises three vibrators with a first of said vibrators disposed proximate said heel portion of said footwear, with a second of said vibrators disposed proximate said toe portion of said footwear and with a third of said vibrators disposed between said first and said second vibrators.

10. A vibrating massage system according to claim 1, further comprising insole means disposed covering said vibrator means.

11. A vibrating massage system according to claim 1, further comprising:

flap means disposed partially covering said arch wall; and fastener means disposed to fasten said flap means to said arch wall and with said electrical connection means connecting said power supply means and said vibrator means disposed between said flap means and said arch wall.

12. A vibrating massage system according to claim 11, in which said fastener means comprises hook and loop fastener means.

13. A vibrating massage system according to claim 1, further comprising perforated insole means.

14. A vibrating massage system according claim 1, in which said sole further comprises a longitudinal air canal connecting said heel portion and said toe portion.

15. A vibrating massage system according to claim 1, in which said sole further comprises a plurality of transverse air canals with said transverse air canals disposed in a transverse direction defined as generally perpendicular to said longitudinal air canal.

16. A vibrating massage system according to claim 13, further comprising perforated filler means disposed between said vibrator means and said insole means.

17. A vibrating massage system according to claim 1, further comprising fastener means disposed fastening said vibrator means to said sole.

* * * * *